US012622749B2

(12) United States Patent
Bartholomeusz

(10) Patent No.: US 12,622,749 B2
(45) Date of Patent: May 12, 2026

(54) HAND PIECE WITH INFORMATION PROJECTION AND IMAGE PROCESSING

(71) Applicant: Lutronic Corporation, Gyeonggi-do (KR)

(72) Inventor: James Bartholomeusz, Beverly Hills, CA (US)

(73) Assignee: Lutronic Corporation, Gyeonggi-do (KR)

( * ) Notice: Subject to any disclaimer, the term of this patent is extended or adjusted under 35 U.S.C. 154(b) by 405 days.

(21) Appl. No.: 18/169,720

(22) Filed: Feb. 15, 2023

(65) Prior Publication Data

US 2024/0268889 A1     Aug. 15, 2024

(51) Int. Cl.
| | |
|---|---|
| *A61B 18/20* | (2006.01) |
| *A61B 18/14* | (2006.01) |
| *A61B 17/00* | (2006.01) |
| *A61B 18/00* | (2006.01) |

(52) U.S. Cl.
CPC ........ *A61B 18/203* (2013.01); *A61B 18/1477* (2013.01); *A61B 2017/00199* (2013.01); *A61B 2018/00452* (2013.01); *A61B 2018/00577* (2013.01); *A61B 2018/00791* (2013.01); *A61B 2018/00904* (2013.01); *A61B 2018/00982* (2013.01)

(58) Field of Classification Search
CPC .............. A61B 18/203; A61B 18/1477; A61B 2017/00199; A61B 2018/00452; A61B 2018/00577; A61B 2018/00791; A61B 2018/00904; A61B 2018/00982
USPC ............................................................ 606/9
See application file for complete search history.

(56) References Cited

U.S. PATENT DOCUMENTS 8,979,871 B2 *   3/2015   Tyc ...................... G01R 33/285
                                              606/130
2012/0109151 A1 *   5/2012   Maier-Hein ........... A61B 34/10
                                              606/130

* cited by examiner

*Primary Examiner* — Aaron F Roane
(74) *Attorney, Agent, or Firm* — Haynes and Boone, LLP

(57) ABSTRACT

A hand piece for dermal therapy is provided that includes a projector configured to project digital information onto the skin of the patient. A clinician may thus monitor the digital information to confirm that the proper therapy parameters are being used or to adjust the dermal therapy based upon the therapy parameters including in the digital information. In addition, the hand piece includes a camera so that image processing may be used to identify features such as a lesion within a treatment area on the skin of the patient. Based on this image processing, the projector may then selectively illuminate the lesion.

12 Claims, 3 Drawing Sheets

HAND PIECE WITH INFORMATION PROJECTION AND IMAGE PROCESSING

TECHNICAL FIELD

This application relates to hand pieces for dermal therapy, and more particularly to a hand piece for dermal therapy with information projection onto the skin of a patient.

BACKGROUND

A variety of dermal treatments involve the use of a hand piece such as hair removal, acne treatment, removal of pigmented lesions or melasma, tattoo removal, and skin tightening. Depending upon the application, the hand piece may be dedicated to the use of RF-excited microneedles or laser therapy. Regardless of the modality and the dermal condition being treated, there is generally a tension between sufficient treatment from the hand piece and insufficient treatment (or excessive treatment). For example, to provide the benefits of a laser peel but with reduced risks, fractional dermal injury (which may also be denoted as fractional laser skin resurfacing) was developed. As implied by the "fractional" designation, a fractional dermal injury does not ablate the entire epidermis of a treatment area. Instead, a pulsed laser as applied by the hand piece forms injured or ablated columns of skin that are separated by healthy tissue.

Radio Frequency (RF) excited microneedles produce a similar fractional dermal injury. As compared to a fractional laser treatment, each microneedle may be insulated such that tissue injury or ablation occurs only around the tip of the microneedle after the microneedle has been inserted into the dermis. Whereas laser fractional therapy tends to produce injured or ablated columns of tissue that extend from the skin surface, RF-excited microneedle therapy tends to produce subdermal injured or ablated regions. But regardless of the type of fractional injury, the presence of healthy, undamaged skin about each injury speeds healing and reduces the risk of infection. Fractional injury thus involves a balancing act between producing sufficient fractional injury and maintaining sufficient amounts of undamaged tissue. Hand piece treatment to remove hair or tattoos faces a similar balancing act between sufficient and insufficient (or excessive) therapy.

There are various factors that affect the balance between sufficient dermal therapy from a hand piece vs. insufficient or excessive therapy. Some important factors may include the skin temperature, the ablation power, the frequency of excitation, and fluence. But a clinician must guide the hand piece so as to treat to the desired areas. The controls or user interface for the treatment factors or variables are contained on a console that attaches to the hand piece through a flexible coupling. But the clinician's attention is directed to the guiding of the hand piece as opposed to monitoring the console. Accordingly, there is a need in the art for improved information availability to the clinician during hand-piece-aided therapy.

SUMMARY

In accordance with an aspect of the disclosure, a laser system for dermal therapy is provided that includes: a laser hand piece including a housing; and a projector extending from an exterior of the housing, the projector being configured to project digital information regarding the dermal therapy onto a skin of a patient.

In accordance with another aspect of the disclosure, an RF-excited microneedle system for dermal therapy is provided that includes: a hand piece including a housing enclosing a plurality of microneedles; and a projector extending from an exterior of the housing, the projector being configured to project digital information regarding the dermal therapy onto a skin of a patient.

In accordance with yet another aspect of the disclosure, a method of treating a patient with a hand piece is provided that includes: positioning the hand piece adjacent to a skin of the patient; and projecting digital information from a projector on the hand piece onto the skin of the patient while treating the skin of the patient with the hand piece.

These and other advantageous features may be better appreciated through the following detailed description.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Figure 1:
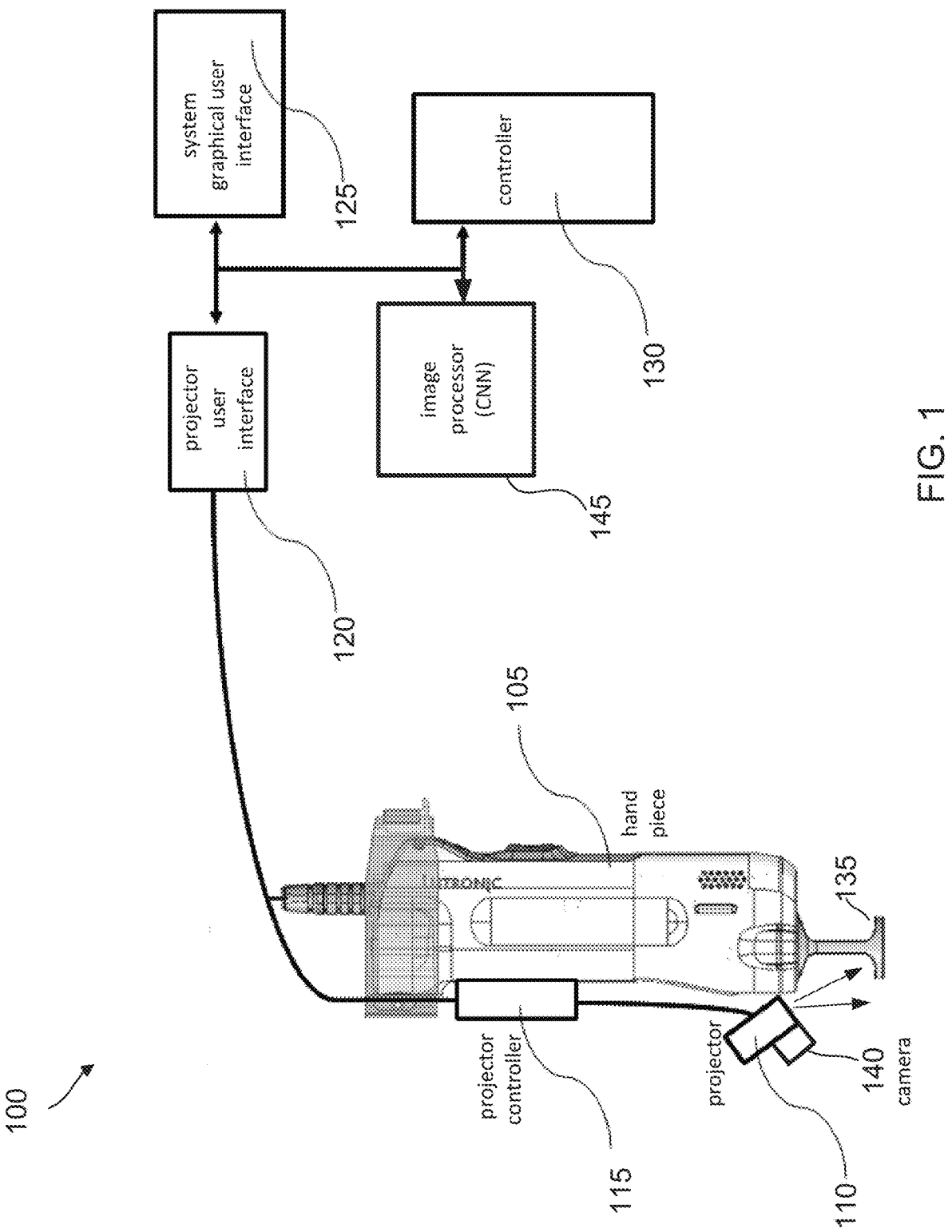
FIG. 1 illustrates a laser system including a hand piece including a projector for projecting digital information onto the skin of a patient in accordance with an aspect of the disclosure.

A variety of dermal treatments involve the use of a hand piece such hair removal, acne treatment, removal of pigmented lesions or melasma, removal of vascular lesions, and tattoo removal. As noted earlier, there is a tension between achieving sufficient dermal therapy and causing insufficient dermal therapy (or excessive therapy). There are various factors that affect this balance between sufficient and insufficient/excessive therapy. These factors are largely common or analogous regardless of the treatment modality. The following discussion will thus first be directed to a generic hand piece treatment that encompasses whatever modality (for example, a laser hand piece or a hand piece for RF-excited microneedles) is used for dermal therapy followed by a discussion of specific examples. Some of the factors that affect whether sufficient dermal therapy is achieved include the skin temperature, the frequency of excitation (e.g., the laser frequency or the RF frequency), the energy delivered per skin area (e.g., the fluence for a laser treatment), and the power of the excitation. In general, existing hand pieces couple to a console that includes a user interface for the setting of the therapy factors. But a clinician may have difficulty in monitoring these parameters since the clinician must attend to the movement or actuation of the hand piece so as to address the area being treated.

To allow the clinician to continue to focus on the hand piece as the clinician treats the patient, an information-projecting hand piece is provided. The hand piece includes a projector (e.g., a pico projector) that projects information on selected factors such as the skin temperature and so on onto the skin of the patient being treated. The patient's skin thus serves as the display for the projector. Advantageously, the displayed information or factors may be projected adjacent to even onto the treatment portion of the skin needing therapy. In this fashion, the clinician is apprised of various parameters or factors that affect the success of dermal therapy.

To provide enhanced therapy, the hand piece is also integrated with a camera configured to image the treatment area. The projector and camera interface with a controller that may be located in the hand piece or in the console. The controller is configured with an image processor such as a convolutional neural network (CNN) to process an image of the treatment area as obtained from the camera. In this fashion, the image processor may identify the lesion being treated (e.g., a pigmented lesion or a vascular lesion). Based upon this identification, the controller may then control the projector to highlight the lesion. Depending upon the application, the lesion may be highlighted with an appropriate color of light to aid the clinician in aiming the laser at the lesion. In this fashion, the clinician may align the aiming beam of the hand piece at the highlighted lesion.

As the camera monitors the resulting ablation of the lesion, the image processor functions in some embodiments to identify the treated portions of the lesion so that the highlighting of the lesion may be adjusted to exclude those portions of the lesion that are already ablated. In addition to the ability to highlight the lesion being ablated, the clinician may select or program what information will be projected adjacent to the treatment area. For example, a console for the hand piece may include a graphical user interface through which the clinician may select or program which factors will be projected onto the patient. The clinician may thus monitor in real time factors such as the fluence, skin temperature, and frequency of excitation. Some example hand pieces will now be discussed in more detail.

An example laser system 100 including a laser hand piece 105 is shown in FIG. 1. A projector 110 such as a pico projector mounts onto the hand piece 105 so as to project information onto both the treatment area and adjacent to the treatment area. Projector 110 is controlled by a projector controller 115. A collimator or spacer 135 separates hand piece 105 from the skin of a patient. During a treatment session, a clinician may position the hand piece 105 so that the spacer 135 rests on the skin treatment area. Projector 110 is configured to project not only onto the skin treatment area but also adjacent to the skin treatment area. A laser such as located within the hand piece 105 may then be actuated to perform a dermal therapy such as fractional injury, hair removal, tattoo removal, eczema and acne treatment, treatment of vascular lesions, reduction of scar tissue redness, and treatment of pigmentation or melasma. A camera 140 on hand piece 105 is aligned to image the treatment area. As noted earlier, an image processor such as a CNN may then process an image of the treatment area so that a lesion or other feature being treated may be highlighted by projector 110. In this fashion, hand piece 105 provides an augmented reality experience for the clinician to provide improved therapy.

In one implementation, the hand piece 105 may be configured for laser fractional injury. In that regard, there are several types of fractional injury. For example, if the tissue being fractionally injured by a pulsing of the laser is heated to 100° C. or greater, the resulting fractional injury is typically denoted as being ablative. If the tissue being fractionally injured by the pulsing of the laser is not heated to 100° C. or greater, the resulting fractional injury is commonly denoted as being non-ablative. There are various forms of non-ablative fractional injury. For example, if the tissue being fractionally injured is heated to greater than 70° C. but less than 100° C., the fractional injury is commonly denoted as a fractional coagulation or tissue necrosis. Should the pulsing of the laser instead heat the tissue being fractionally injured to less than 70° C. but above 40° C., the fractional injury is often denoted as non-immediately destructive tissue heating.

Figure 2:
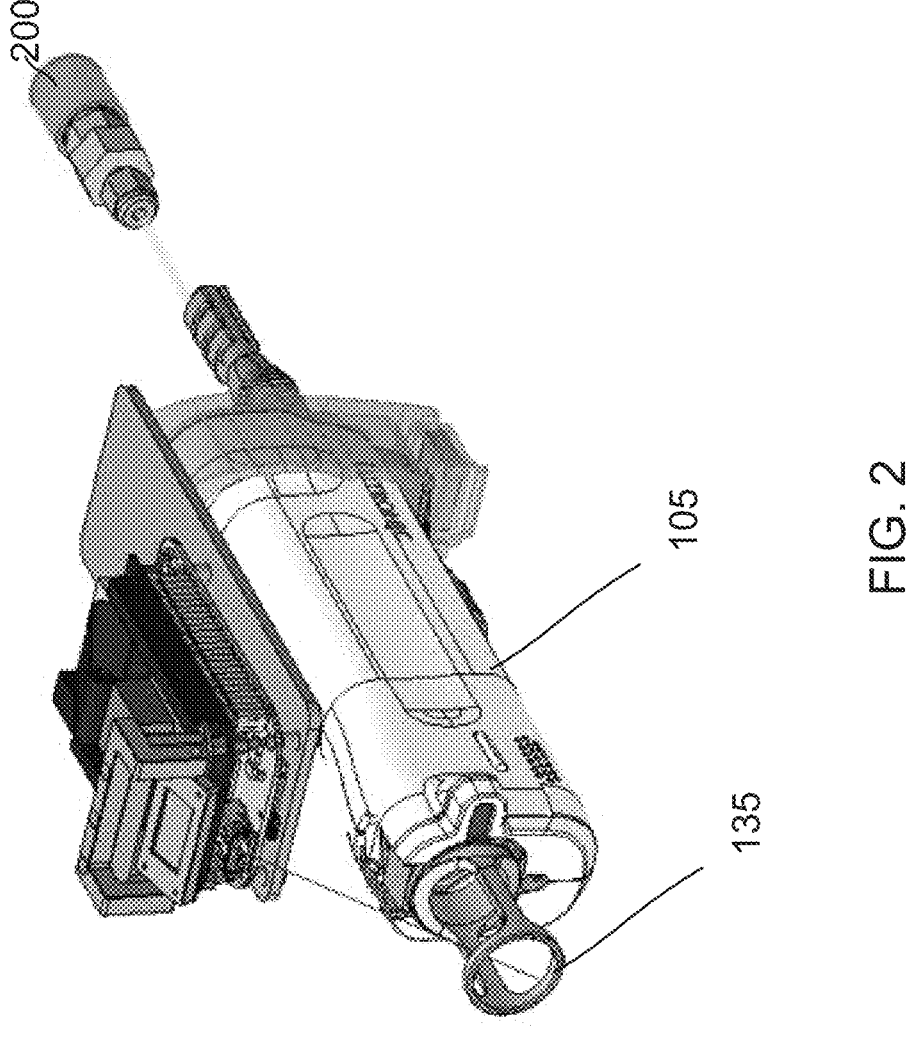
FIG. 2 is a perspective view of the hand piece of FIG. 1.

Skin temperature and laser fluence (such as measured in Joules/centimeter squared) are some factors that control what type of fractional injury is being produced. To control which factors or treatment parameters are projected onto or adjacent the treatment area on the skin of a patient from projector 110, system 100 may include a projector user interface 120 through which a user may select which factors are projected as controlled by controller 115. In addition, system 100 may include a system graphical user interface 125 for general control of laser system 100 such as the laser frequency and so on. It will be appreciated that user interfaces 120 and 125 may be combined into a single user interface. A controller 130 controls system 100 according to inputs from user interfaces 120 and 125. Controller 130 also interfaces with an image processor (CNN) 145 for the processing of the treatment area image taken by camera 140. User interfaces 120 and 125 and controller 130 may be located in a console (not illustrated) that couples to hand piece 105 through a flexible conduit 200 a portion of which is shown in FIG. 2. Referring again to FIG. 1, it will thus be appreciated that the coupling between projector controller 115 and projector user interface 120 would actually be contained within flexible conduit 200.

To speed the training of the CNN 145, a transfer learning technique may be used in which a pre-existing commercial-off-the-shelf (COTS) CNN such as the Matlab-based "Alexnet" which has been trained on an ImageNet database having 1.2 million training images and 1000 object categories. The following discussion concerns the processing of one image from a single camera 140 on the hand piece 105 but it will be appreciated that the image processing disclosed herein is readily adapted to the processing of multiple images from a corresponding plurality of cameras.

With regard to training the CNN 145, various images of skin lesions during ablation may be partitioned into categories of healthy skin, untreated lesion, and ablated lesion. The images to be classified into these categories are added to an image data base used to pretrain the COTS CNN 145. Upon CNN processing, each image is classified (labeled) into the three categories of healthy skin, lesion, and ablated lesion with some probability. Only frames satisfying a probability threshold (e.g., 70%) are deemed to be correctly labeled. Should the CNN processing result in a classification below the probability threshold, the frame is classified as a no detection (ND). There are thus four labels that may be assigned to an image: healthy skin, lesion, ablated lesion, and ND.

A recursive training process may be used to enhance the resulting classification accuracy. In particular, a human operator may review the classification. Should an image be falsely labelled (a portion of the image classified as healthy skin, lesion, or ablated lesion with a probability greater than the probability threshold), it is removed from the training database. In addition, some ND classifications may be improper. Should there be image partitions that rightfully should have been classified as healthy skin, lesion, or ablated lesion but were classified as ND by the CNN 145, they may be properly classified in a correction step by the human operator. The recursive training of CNN 145 would thus continue until all the images have been properly identified. The resulting trained CNN 145 may then be used to provide an augmented reality session for the operator so that projector 110 highlights the untreated portion of a lesion being ablated in the treatment area.

Figure 3:
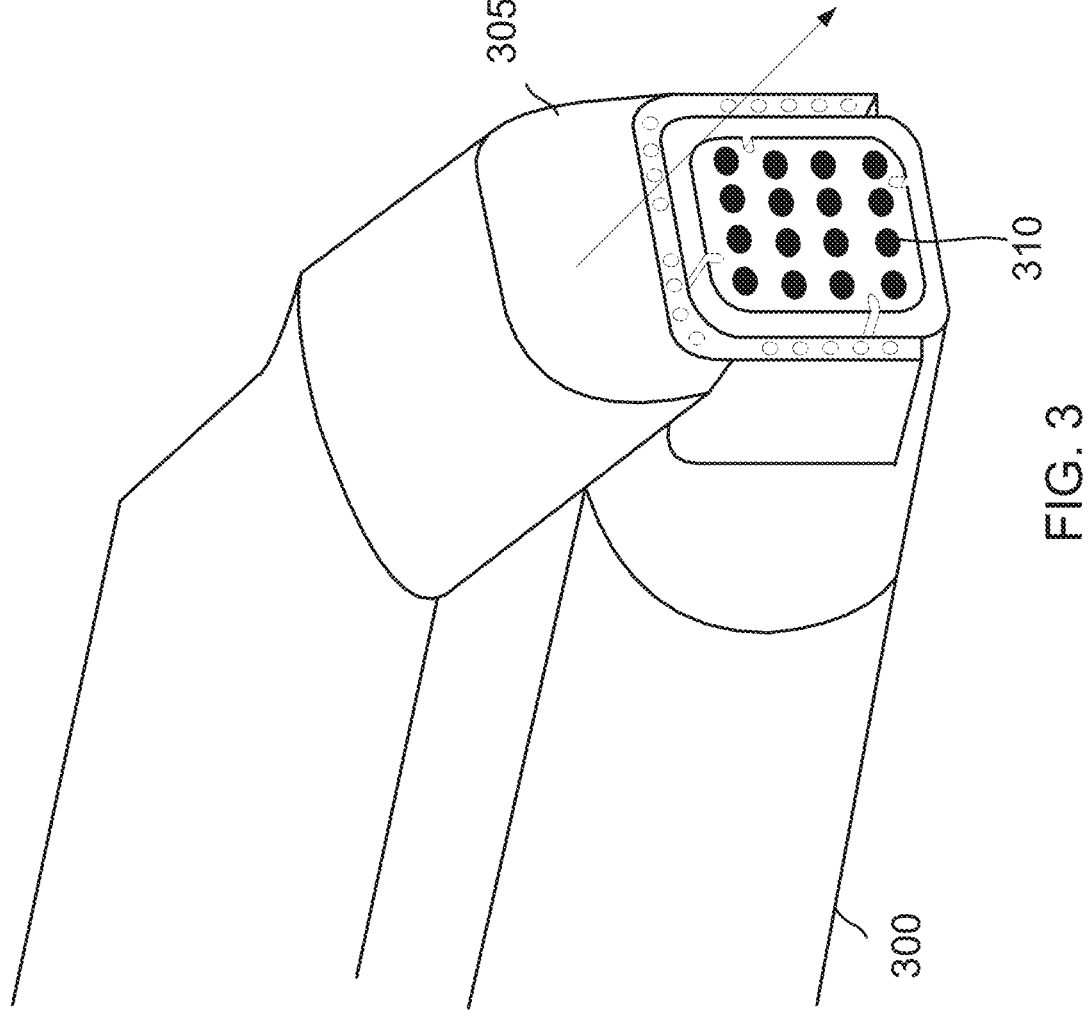
FIG. 3 is a perspective view of an RF-excited microneedle hand piece including a projector for projecting digital information onto the skin of a patient in accordance with an aspect of the disclosure.

A projector may also be advantageously included within a hand piece for RF excitation of a microneedle array. An example microneedle hand piece 300 is shown in FIG. 3. Hand piece 300 includes a housing that encloses a plurality of microneedles that may be actuated through holes 310. With the microneedles inserted into the skin of a patient, the microneedles are energized with an RF signal to apply the desired fractional injury or ablation. To assist the clinician during the microneedle therapy, hand piece 300 includes a projector 305 such as a pico projector that projects digital information onto the skin of the patient. For example, projector 305 may project a pulse on-time of the RF energy, the skin temperature, a mode status such as whether the microneedle system is in a setup mode or an active mode, and a power of the RF energy.

Those of some skill in this art will by now appreciate and depending on the particular application at hand, many modifications, substitutions and variations can be made in and to the materials, apparatus, configurations and methods of use of the devices of the present disclosure without departing from the scope thereof. In light of this, the scope of the present disclosure should not be limited to that of the particular embodiments illustrated and described herein, as they are merely by way of some examples thereof, but rather, should be fully commensurate with that of the claims appended hereafter and their functional equivalents.

I claim:

1. An RF-excited microneedle system for dermal therapy, comprising:
   a hand piece including a housing enclosing a plurality of microneedles that may be actuated through holes in the housing; and
   a projector extending from an exterior of the housing, the projector being configured to project digital information regarding parameters of the dermal therapy onto a skin of a patient.

2. The RF-excited microneedle system of claim 1, wherein the projector comprises a pico projector.

3. The RF-excited microneedle system of claim 1, further comprising:
   a user interface for controlling a selection of the digital information.

4. The RF-excited microneedle system of claim 1, wherein the parameters of the dermal therapy include a pulse on-time of the RF energy for the RF-excited microneedle system.

5. The RF-excited microneedle system of claim 1, wherein the parameters of the dermal therapy include a temperature of the skin of the patient.

6. The RF-excited microneedle system of claim 1, wherein the parameters of the dermal therapy include a mode status of whether the RF-excited microneedle system is in a setup mode or in an active mode.

7. The RF-excited microneedle system of claim 1, wherein the parameters of the dermal therapy include a power of the RF energy for the RF-excited microneedle system.

8. A method of treating a patient with a hand piece, comprising:
   positioning the hand piece adjacent to a skin of the patient; and
   projecting digital information regarding parameters of a dermal therapy administered by the hand piece, wherein the projecting of the digital information is produced from a projector on the hand piece onto the skin of the patient during the dermal therapy.

9. The method of claim 8, wherein the dermal therapy comprises projecting a laser beam from the hand piece onto the skin of the patient.

10. The method of claim 8, wherein the dermal therapy comprises inserting a plurality of microneedles from the hand piece into the skin of the patient and exciting the inserted microneedles with RF energy.

11. The method of claim 8, further comprising:
   imaging a treatment portion of the skin of the patient to provide an image;
   processing the image to identify a lesion within the treatment portion; and
   illuminating the lesion through the projector responsive to the processing of the image.

12. The method of claim 11, further comprising:
   limiting an illumination of the lesion through the projector to exclude ablated portions of the lesion.

* * * * *